(12) United States Patent
Forster

(10) Patent No.: US 10,913,594 B2
(45) Date of Patent: Feb. 9, 2021

(54) SMART EJECTION TRAYS FOR USE WITH MEDICATION CONTAINERS

(71) Applicant: Avery Dennison Retail Information Services, LLC, Mentor, OH (US)

(72) Inventor: Ian James Forster, Chelmsford-Essex (GB)

(73) Assignee: Avery Dennison Retail Information Services, LLC, Mentor, OH (US)

( * ) Notice: Subject to any disclaimer, the term of this patent is extended or adjusted under 35 U.S.C. 154(b) by 0 days.

(21) Appl. No.: 14/793,335

(22) Filed: Jul. 7, 2015

(65) Prior Publication Data

US 2017/0008689 A1   Jan. 12, 2017

(51) Int. Cl.
| | | |
|---|---|---|
| *A61J 1/03* | (2006.01) | |
| *B65D 83/04* | (2006.01) | |
| *A61J 7/04* | (2006.01) | |
| *A61J 7/00* | (2006.01) | |
| *G06F 19/00* | (2018.01) | |

(52) U.S. Cl.
CPC ........ *B65D 83/0409* (2013.01); *A61J 7/0069* (2013.01); *A61J 7/0436* (2015.05); *G06F 19/3418* (2013.01); *G06F 19/3462* (2013.01); *A61J 1/03* (2013.01); *A61J 2200/30* (2013.01)

(58) Field of Classification Search
CPC .. A61J 1/03; A61J 7/0076; A61J 1/035; A61J 2200/30; G07F 11/62; G07F 17/0092
USPC .................................. 221/25, 69, 89, 30, 31
See application file for complete search history.

(56) References Cited

U.S. PATENT DOCUMENTS

| | | |
|---|---|---|
| 4,429,792 A | 2/1984 | Machbitz |
| 4,526,474 A | 7/1985 | Simon |
| 4,617,557 A | 10/1986 | Gordon |
| 4,660,991 A | 4/1987 | Simon |
| 5,181,189 A | 1/1993 | Hafner et al. |
| 5,313,439 A | 5/1994 | Albeck |
| 5,412,372 A | 5/1995 | Parkhurst et al. |
| 5,642,731 A | 7/1997 | Kehr et al. |

(Continued)

FOREIGN PATENT DOCUMENTS

| | | |
|---|---|---|
| CN | 1314863 | 9/2001 |
| CN | 1395916 | 2/2003 |

(Continued)

OTHER PUBLICATIONS

International Search Report and Written Opinion dated Mar. 11, 2016 for International Application No. PCT/US2015/064888 filed Dec. 10, 2015.

(Continued)

*Primary Examiner* — Timothy R Waggoner

(57) ABSTRACT

An ejection tray is provided for use in combination with a medication container including a medication-containing cell. The tray includes a frame configured to receive at least a portion of the medication container. An actuator is movably associated with the frame to eject the medication from the cell. A switch is associated with the frame and configured to change from a first state to a second state upon the actuator being moved to eject the medication from the cell. A host processor is associated with the frame and is electrically coupled or selectively coupled to the switch. The host processor is programmed to detect a change in the state of the switch.

17 Claims, 5 Drawing Sheets

(56) References Cited

U.S. PATENT DOCUMENTS

| | | | |
|---|---|---|---|
| 5,836,474 A | 11/1998 | Wessberg | |
| 5,871,831 A | 2/1999 | Zeiter et al. | |
| 5,905,653 A | 5/1999 | Higham et al. | |
| 6,048,087 A | 4/2000 | Laurent et al. | |
| 6,294,999 B1 | 9/2001 | Yarin et al. | |
| 6,339,732 B1 | 1/2002 | Phoon et al. | |
| 6,411,567 B1 | 6/2002 | Niemiec et al. | |
| 6,664,887 B1 | 12/2003 | Fuchs | |
| 6,824,739 B1 | 11/2004 | Arney et al. | |
| 6,961,285 B2 | 11/2005 | Niemiec et al. | |
| 6,973,371 B1 | 12/2005 | Benouali | |
| 7,252,208 B1* | 8/2007 | Alvino | B65D 83/0463 221/28 |
| 7,298,343 B2 | 11/2007 | Forster et al. | |
| 7,828,147 B2 | 11/2010 | Caracciolo et al. | |
| 8,072,334 B2 | 12/2011 | Forster et al. | |
| 8,704,716 B2 | 4/2014 | Kato et al. | |
| 8,751,039 B1* | 6/2014 | Macoviak | A61J 7/0076 700/236 |
| 8,960,440 B1* | 2/2015 | Kronberg | A61J 1/035 206/531 |
| 9,172,130 B2 | 10/2015 | Forster | |
| 2001/0028308 A1* | 10/2001 | De La Huerga | A61M 5/14212 340/573.1 |
| 2002/0017996 A1* | 2/2002 | Niemiec | A61J 7/0481 340/573.1 |
| 2002/0111542 A1 | 8/2002 | Warkentin et al. | |
| 2003/0007421 A1 | 1/2003 | Niemiec et al. | |
| 2003/0046563 A1 | 3/2003 | Ma et al. | |
| 2003/0063524 A1 | 4/2003 | Niemiec et al. | |
| 2003/0111479 A1* | 6/2003 | Taneja | B65D 83/0454 221/25 |
| 2003/0121930 A1* | 7/2003 | Layer | A61J 7/0481 221/25 |
| 2004/0078879 A1 | 4/2004 | Zach et al. | |
| 2005/0062238 A1 | 3/2005 | Broadfield et al. | |
| 2005/0162255 A1 | 7/2005 | Goel et al. | |
| 2005/0162979 A1 | 7/2005 | Ostergaard et al. | |
| 2005/0237222 A1 | 10/2005 | Bogash et al. | |
| 2005/0241983 A1 | 11/2005 | Snyder et al. | |
| 2005/0252924 A1 | 11/2005 | Pieper et al. | |
| 2005/0256830 A1 | 11/2005 | Siegel et al. | |
| 2006/0061472 A1 | 3/2006 | Lovoi et al. | |
| 2006/0071774 A1 | 4/2006 | Brown et al. | |
| 2006/0079996 A1 | 4/2006 | Benouali | |
| 2006/0124656 A1 | 6/2006 | Fopovich, Jr. | |
| 2006/0144749 A1 | 7/2006 | Arnold et al. | |
| 2006/0202830 A1 | 9/2006 | Scharfeld et al. | |
| 2007/0018819 A1 | 1/2007 | Streeb et al. | |
| 2007/0023316 A1 | 2/2007 | Coe et al. | |
| 2007/0246396 A1 | 10/2007 | Brollier | |
| 2008/0012579 A1 | 1/2008 | Kuhns et al. | |
| 2008/0223936 A1 | 9/2008 | Mickle et al. | |
| 2009/0210247 A1 | 8/2009 | Chudy et al. | |
| 2009/0218846 A1 | 9/2009 | Nguyen et al. | |
| 2009/0278626 A1 | 11/2009 | Lee | |
| 2009/0278688 A1 | 11/2009 | Tuttle | |
| 2009/0294521 A1 | 12/2009 | De La Huerga et al. | |
| 2009/0309704 A1 | 12/2009 | Chang et al. | |
| 2010/0089791 A1 | 4/2010 | Rosenbaum et al. | |
| 2010/0094455 A1 | 4/2010 | Dehlin et al. | |
| 2010/0114367 A1 | 5/2010 | Barrett et al. | |
| 2010/0187243 A1 | 7/2010 | Layer et al. | |
| 2010/0314282 A1 | 12/2010 | Bowers | |
| 2011/0037485 A1 | 2/2011 | Kiy | |
| 2012/0003928 A1 | 1/2012 | Geboers et al. | |
| 2012/0010939 A1 | 1/2012 | Krishnamoorth et al. | |
| 2012/0056000 A1 | 3/2012 | Shores | |
| 2012/0109397 A1 | 5/2012 | Shim et al. | |
| 2012/0125994 A1 | 5/2012 | Heath et al. | |
| 2012/0156992 A1 | 6/2012 | Walker et al. | |
| 2012/0228192 A1 | 9/2012 | Niven | |
| 2012/0229279 A1 | 9/2012 | Conley et al. | |
| 2013/0022007 A1 | 2/2013 | Paavilainen | |
| 2013/0044007 A1 | 2/2013 | Paavilainen et al. | |
| 2013/0195326 A1 | 8/2013 | Bear et al. | |
| 2013/0222135 A1 | 8/2013 | Stein et al. | |
| 2013/0285681 A1 | 10/2013 | Wilson et al. | |
| 2014/0039445 A1 | 2/2014 | Austin et al. | |
| 2014/0048442 A1 | 2/2014 | Maijala et al. | |
| 2014/0052467 A1 | 2/2014 | Maijala et al. | |
| 2014/0166529 A1 | 6/2014 | Fung et al. | |
| 2014/0243749 A1 | 8/2014 | Edwards et al. | |
| 2014/0262918 A1 | 9/2014 | Chu | |
| 2014/0288942 A1 | 9/2014 | Blochet | |
| 2014/0340198 A1 | 11/2014 | Kawase et al. | |
| 2014/0354433 A1 | 12/2014 | Buco et al. | |
| 2014/0360898 A1 | 12/2014 | Kantor et al. | |
| 2015/0032533 A1 | 1/2015 | Raab et al. | |
| 2015/0048100 A1* | 2/2015 | Dickie | A61J 7/0481 221/1 |
| 2015/0048102 A1 | 2/2015 | Dickie et al. | |
| 2015/0048170 A1 | 2/2015 | Forster | |
| 2015/0339566 A1 | 2/2015 | Forster | |
| 2015/0066204 A1 | 3/2015 | Patel et al. | |
| 2015/0274402 A1 | 10/2015 | Elliott | |
| 2015/0283036 A1 | 10/2015 | Aggarwal et al. | |
| 2015/0286852 A1 | 10/2015 | Sengstaken, Jr. | |
| 2015/0325336 A1 | 11/2015 | Maples | |
| 2015/0347712 A1 | 12/2015 | Flori et al. | |
| 2015/0347713 A1 | 12/2015 | Seeger | |
| 2015/0356845 A1 | 12/2015 | Forster | |
| 2016/0019452 A1 | 1/2016 | Forster | |
| 2016/0106622 A1 | 4/2016 | Van De Wouw et al. | |
| 2016/0132661 A1 | 5/2016 | Dixit et al. | |
| 2016/0137380 A1 | 5/2016 | Kosaka | |
| 2016/0143807 A1 | 5/2016 | Ika et al. | |
| 2016/0143809 A1 | 5/2016 | Webster et al. | |
| 2016/0147976 A1 | 5/2016 | Jain | |
| 2016/0158108 A1 | 6/2016 | Gofer et al. | |
| 2016/0158109 A1 | 6/2016 | Nova et al. | |
| 2016/0367435 A1 | 12/2016 | Ahmadi | |
| 2017/0011240 A1 | 1/2017 | Forster | |
| 2017/0053095 A1 | 2/2017 | Blum et al. | |
| 2017/0165151 A1 | 6/2017 | Schmid et al. | |
| 2017/0337157 A1 | 11/2017 | Rothschild | |
| 2018/0012117 A1 | 1/2018 | Forster | |
| 2018/0042105 A1 | 2/2018 | Anderson | |
| 2018/0156756 A1 | 6/2018 | Forster | |
| 2018/0319519 A1 | 11/2018 | Stange et al. | |

FOREIGN PATENT DOCUMENTS

| | | |
|---|---|---|
| CN | 1568171 | 1/2005 |
| CN | 101309846 | 11/2008 |
| CN | 202046575 | 11/2011 |
| CN | 104135985 | 11/2014 |
| EP | 1758050 | 2/2007 |
| EP | 2026253 | 2/2009 |
| NL | 151311 | 3/1977 |
| WO | 2006002667 | 1/2006 |
| WO | 2008000279 | 1/2008 |
| WO | 2009116108 | 9/2009 |
| WO | WO-2009116108 A1 * | 9/2009 ............ A61J 7/0481 |

OTHER PUBLICATIONS

International Search Report and Written Opinion dated Dec. 5, 2016 for International Application No. PCT/US2016/039714 filed Jun. 28, 2016.

International Search Report and Written Opinion dated Oct. 4, 2016 for International Application No. PCT/US2016/039720 filed Jun. 28, 2016.

International Search Report dated Sep. 29, 2015 for international Application No. PCT/US2015/038763 filed Jul. 1, 2015.

international Preliminary Report on Patentability and Written Opinion dated Jan. 10, 2017 for International Application No. PCT/US2015/038763 filed Jul. 1, 2015.

International Preliminary Report on Patentability dated Jun. 13, 2017 for International Application No. PCT/US2015/064888 filed Dec. 10, 2015.

(56) References Cited

OTHER PUBLICATIONS

International Search Report and Written Opinion dated Sep. 28, 2017 for International Application No. PCT/US2017/041125 filed Jul. 7, 2017.
International Preliminary Report on Patentability dated Jan. 8, 2019 for International Application No. PCT/US2017/041125 filed Jul. 7, 2017.
International Preliminary Report on Patentability dated Jan. 18, 2018 issued in corresponding IA No. PCT/US2016/039714 filed Jun. 28, 2016.
International Preliminary Report on Patentability dated Jan. 9, 2018 issued in corresponding IA No. PCT/US2016/039720 filed Jun. 28, 2016.

* cited by examiner

SMART EJECTION TRAYS FOR USE WITH MEDICATION CONTAINERS

BACKGROUND

Field of the Disclosure

The present subject matter relates to monitoring the medication intake of a subject. More particularly, the present subject matter relates to smart ejection trays for use in combination with medication containers for monitoring the medication intake of a subject.

Description of Related Art

Frequently, a doctor or medical care provider will issue instructions to a subject to periodically ingest one or more doses of medication in the form of a pill or tablet or capsule or the like as part of a treatment regimen. Unless the subject is within a facility under the control of the doctor or medical care provider (e.g., a hospital or nursing home), it can be difficult for the doctor or medical care provider to know whether the subject is ingesting the prescribed medication at the proper times. Accordingly, it would be advantageous to provide systems and methods that increase the likelihood that a subject will properly follow a prescribed medication routine.

SUMMARY

There are several aspects of the present subject matter that may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as may be set forth in the claims appended hereto.

In one aspect, an ejection tray is provided for use in combination with a medication container including a medication-containing cell. The tray includes a frame configured to receive at least a portion of the medication container. An actuator is movably associated with the frame to eject the medication from the cell. A switch is associated with the frame and configured to change from a first state to a second state upon the actuator being moved to eject the medication from the cell. A host processor is associated with the frame and is electrically coupled or selectively coupled to the switch. The host processor is programmed to detect a change in the state of the switch.

DESCRIPTION OF THE ILLUSTRATED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

According to an aspect of the present disclosure, a smart ejection tray 10 may be used in combination with a medication container 12 (FIGS. 1 and 2) to better assure that a subject abides by a prescribed medication routine. As will be described in greater detail herein, the ejection tray 10 may be configured to communicate with a separate electronic device, which may allow a doctor or medical care provider to monitor medication compliance. Preferably, the ejection tray 10 is a durable, reusable component, while the medication container 12 is a single-use, disposable component, but it is also within the scope of the present disclosure for the ejection tray 10 to be a single- or limited-use device and for the medication container 12 to be reusable, for both components to be durable and reusable, or for both components to be configured for single use or only limited reuse.

Figure 2:
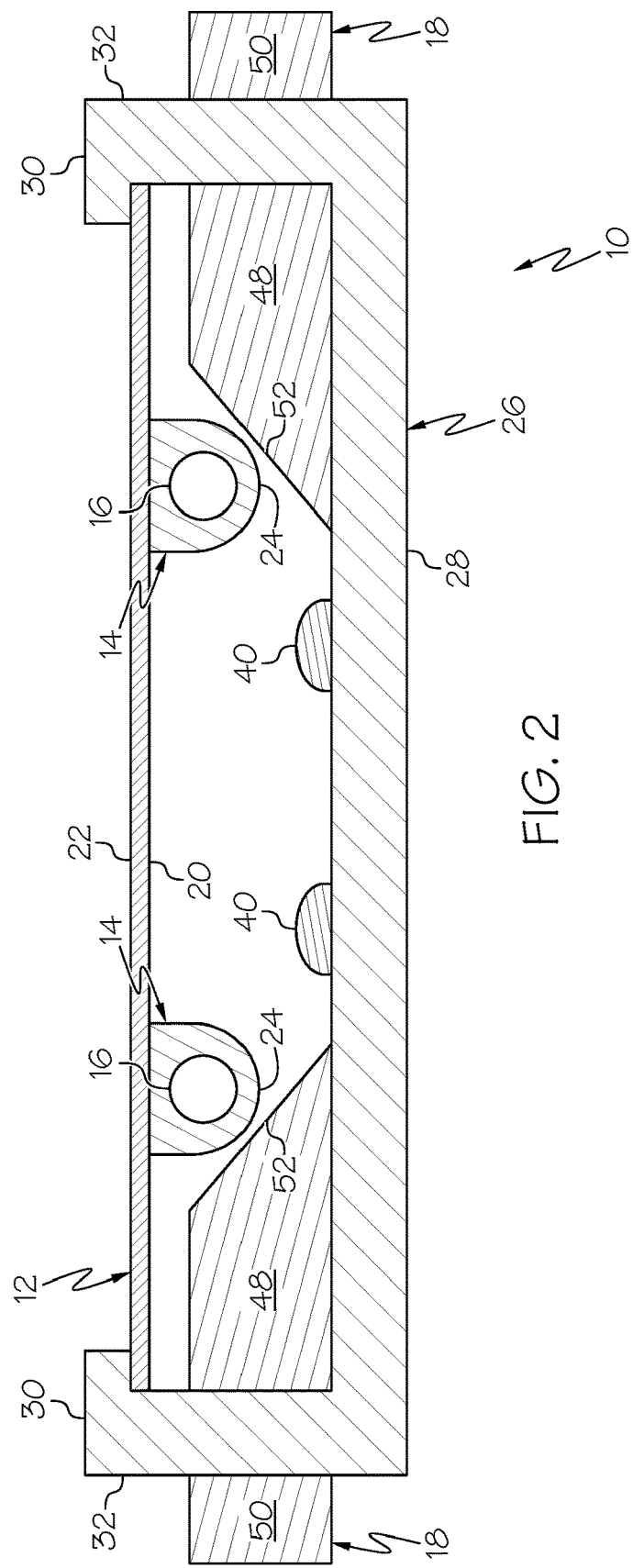
FIG. 2 is a front cross-sectional view of the ejection tray and medication container of FIG. 1.

The medication container 12 includes at least one cell 14 in which a dose of medication 16 is contained (FIG. 2). Preferably, the medication container 12 includes a plurality of identical cells 14, but it is also within the scope of the present disclosure for a medication container 12 to include differently configured cells or only one cell.

Each cell 14 may be formed of any suitable material but, in one embodiment, each cell is formed of a thin plastic material or another deformable material. In particular, it may be advantageous for the cells 14 to be formed of a material that is generally rigid, but sufficiently deformable that an actuator or ejector wedge 18 of the tray 10, when brought into contact with the cell 14 (as will be described in greater detail), deforms the cell 14. In a preferred embodiment, the body of the medical container 12 takes the general form of a blister pack, with a thin plastic sheet 20 (FIG. 2) being provided with a plurality of vacuum-formed depressions or formations that each defines a cell 14 for receiving a dose of medication 16. While it may be preferred for a medication container having a plurality of cells to be provided with a single plastic sheet that is formed to define all of the cells, it is also within the scope of the present disclosure for the cells of a single medication container to be separately or non-integrally formed.

Each cell 14 is preferably closed or overlaid by a cover 22 through which medication 16 within the cell 14 may be accessed. In one embodiment, the cover 22 is a thin sheet of material, such as a metallic foil or an at least partially light-transmissive (e.g., transparent or translucent) sheet, which may be broken to allow medication 16 to pass out of the cell 14. In such an embodiment, a base 24 of the cell 14 may be pressed toward the frangible cover 22 by a user operating an associated actuator 18 of the tray 10 (as will be described in greater detail) until the force on the cover 22 exceeds the strength of the cover 22, at which point the cover 22 breaks and the medication 16 may be removed or is ejected from the cell 14.

If the medication container 12 is provided with a plurality of cells 14, it may be preferred for a single cover 22 to overlay all of the cells 14, but it is also within the scope of the present disclosure for two or more cells of the same medication container to be provided with separate covers. For example, in one embodiment, different cells are each overlaid by separate, non-frangible (e.g., hinged) covers.

Figure 1:
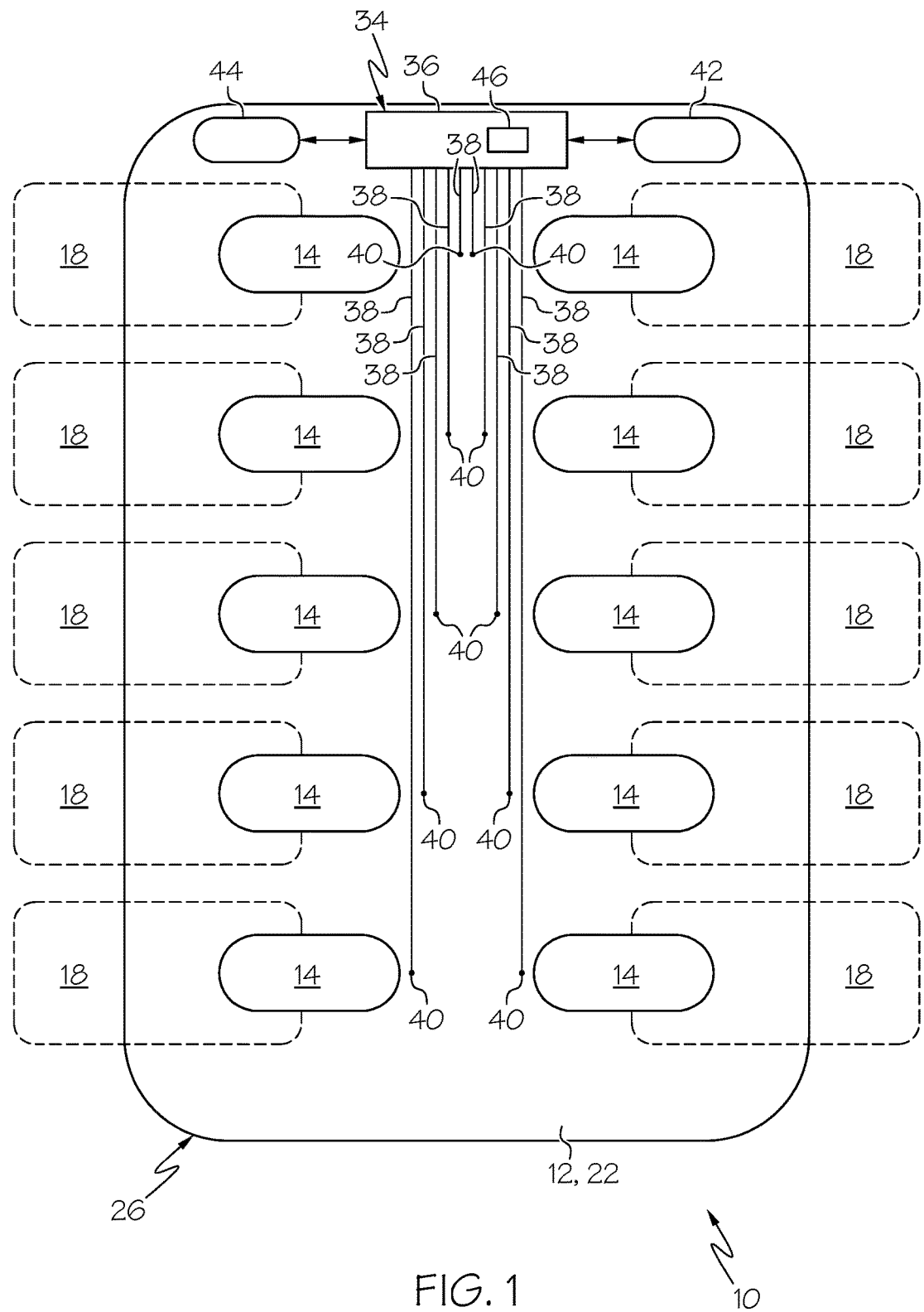
FIG. 1 is a diagrammatic top plan view of a smart ejection tray and associated medication container according to an aspect of the present disclosure.

In the embodiment of FIGS. 1 and 2, the tray 10 is defined by a frame 26. The frame 26 may be formed of any suitable material, which is preferably relatively rigid and non-conductive (e.g., a plastic material). The frame 26 defines an open interior or cavity or compartment to receive at least a portion of an associated medication container 12. In the illustrated embodiment, the frame 26 includes a bottom surface 28 and a top surface 30 (which are substantially horizontal in the orientation of FIG. 2), with a pair of lateral sidewalls 32 (which are substantially vertical in the orientation of FIG. 2) extending between the bottom and top surfaces 28 and 30. The configuration of the frame 26 allows for the medication container 12 to be slid or otherwise moved into the open interior of the frame 26, being held in place between the bottom and top surfaces 28 and 30 of the frame 26 and between the lateral sidewalls 32.

It should be understood that the illustrated embodiment is merely exemplary and that the frame 26 may be differently configured without departing from the scope of the present disclosure. For example, the medication container 12 can take the form of a standard blister pack or other previously available and/or existing container or containers having some or all of the basic features described in one of a variety of available configurations, sizes, thicknesses of various walls and/or materials of construction. Also, the tray 10 can be sized, configured and made of materials such that the tray 10 clips onto or around the medication container 12, whether of a standard type or of a type specially designed for use in combination with the tray 10. Further, the frame 26 can achieve or contribute to such clip onto or around functions. The clipping function typically has the ability to securely capture the medication container 12, whether by siding action, snapping action, or a combination thereof.

A circuit 34 is incorporated into or otherwise associated with the frame 26 of the ejection tray 10 (FIG. 1). The illustrated circuit 34 includes a host processor 36, which is electrically coupled (e.g., via a wire or comparable conductor 38) or selectively coupled to a switch 40. The switch 40 is configured to change from a first state to a second state (and, in one embodiment, back to the first state from the second state), which states will be described in greater detail herein. The circuit 34 may further include a battery or supercapacitor or power source 42 electrically coupled to the host processor 36 to provide power to the other components of the circuit 34, along with a communication device 44 (e.g., an antenna or USB port) configured to communicate with a separate electronic device, as will be described in greater detail herein. The circuit 34 may include additional components (e.g., an internal, real-time clock 46) without departing from the scope of the present disclosure.

In the embodiment of FIGS. 1 and 2, a medication container 12 associated with the tray 10 includes a plurality of medication-containing cells 14 (ten in the illustrated embodiment), with the circuit 34 including a plurality of switches 40. FIG. 1 shows the individual switches 40 electrically coupled or selectively coupled to the host processor 36 by individual conductors 38, but it is also within the scope of the present disclosure for the various switches 40 to be electrically coupled or selectively coupled to the host processor 36 according to a different conductive arrangement. The circuit 34 preferably includes the same number of switches 40 as the medication container 12 includes cells 14, but it is also within the scope of the present disclosure for the number of cells 14 and switches 40 to be different.

Most preferably, the number of cells 14 and switches 40 is the same, with each switch 40 associated with a different one of the cells 14. Each switch 40 is preferably paired with a different actuator 18 of the ejection tray 10, thereby providing a switch-actuator-cell combination. Each actuator 18 is movably associated with the frame 26 of the tray 10, such that the actuator 18 may be moved with respect to the frame 26. The way in which an actuator 18 is movably associated with the frame 26 may vary without departing from the scope of the present disclosure, provided that the actuator 18 may be moved in a way so as to allow the medication 16 of an associated cell 14 to be removed from the cell 14 or so as to cause the medication 16 to be ejected from that cell 14. In the illustrated embodiment, each actuator 18 extends through a different one of a plurality of openings or passages defined in the sidewalls 32 of the frame 26, with an inside or internal portion 48 of the actuator 18 positioned within the bounds of the frame 26 (e.g., within the open interior of the frame 26) and with an outside or external portion 50 of the actuator 18 positioned outside of the bounds of the frame 26. The internal portion 48 of the actuator 18 may be initially spaced or separated from the associated cell 14 or, if initially in contact with the associated cell 14, in contact with the cell 14 without deforming the cell 14.

In the embodiment of FIGS. 1 and 2, the actuators 18 are generally wedge-shaped, with the internal portion 48 of each actuator 18 being provided with a ramped or angled or inclined surface 52, which faces the open interior of the frame 26 and is angled with respect to horizontal and vertical (in the orientation of FIG. 2). The illustrated angled surface 52 is substantially planar, but it is within the scope of the present disclosure for the angled surface 52 to be non-planar (e.g., curved).

The illustrated angled surface 52 has one portion (illustrated as a bottom or lower portion) positioned closer to the associated switch 40 or to the center of the tray 10 and another portion (illustrated as a top or upper portion) positioned farther from the associated switch 40 or center of the tray 10. The opening or passage in the sidewall 32 through which the actuator 18 extends is configured to allow the actuator 18 to be moved toward and away from the associated cell 14 to progressively cause a greater portion of the angled surface 52 to come into contact with the cell 14. By the illustrated configuration, moving the actuator 18 toward the associated cell 14 causes the angled surface 52 to contact and deform the cell 14, advancing the medication 16 contained within the cell 14 toward the cover 22 until the medication 16 is ultimately pressed through the cover 22. The illustrated actuators 18 are configured to move (e.g., by sliding) in a common, substantially horizontal plane (in the orientation of FIG. 2) by pressing or otherwise applying a force to the external portion 50 of the actuator 18 in a direction toward the associated cell 14. However, it is also within the scope of the present disclosure for different actuators 18 of a single tray 10 to move in different planes and/or in different ways. Additionally, the actuators 18 of a single tray 10 may be differently configured, although it may be preferred for all of the actuators 18 to be substantially identical, as illustrated.

Moving an actuator 18 to the extent that the medication 16 of the associated cell 14 may be removed from or is ejected from the cell 14 also causes the associated switch 40 to change from the first state to the second state. In the first state, the switch 40 indicates that the medication 16 in the associated cell 14 has not yet been accessed. In the second state, the switch 40 indicates that the medication 16 in the associated cell 14 has been accessed. The way in which the switch 40 changes from the first state to the second state may vary without departing from the scope of the present disclosure. In one embodiment in which the switch 40 is permanently coupled to the host processor 36, the switch 40 is configured to transmit different signals or to have different electrical properties detected by the host processor 36 in the first and second states. In such an embodiment, the actuator 18 may cause a change in the state of the switch 40 either by physically contacting the switch 40 or without physically contacting the switch 40.

In an alternative embodiment in which the switch 40 is selectively coupled to the host processor 36, the switch 40 may initially be out of communication with the host processor 36 in the first state (e.g., out of contact with the associated conductor 38) and then moved into communication with the host processor 36 by the actuator 18 to change the switch 40 to the second state (e.g., by the actuator 18 physically contacting and moving the switch 40 into contact with the associated conductor 38). In yet another embodiment in which the switch 40 is selectively coupled to the host processor 36, there may be a gap in the conductor 38 between the switch 40 and the host processor 36, with the actuator 18 having a conductive portion (or moving a conductive element) that bridges the gap to place the switch 40 in the second state, in which it may communicate with the host processor 36. Other relationships between an actuator 18 and associated switch 40 for changing the switch 40 from a first state to a second state (and, optionally, back to the first state from the second state) may also be employed without departing from the scope of the present disclosure.

Thus, in use, a subject or user presses or otherwise advances the external portion 50 of the actuator 18 toward the associated cell 14 to eject the medication 16 in the cell 14 from the cell 14. So ejecting the medication 16 changes the switch 40 associated with the cell 14 to change from the first state (signifying that the medication 16 has not yet been accessed) to the second state (signifying that the medication 16 has been accessed). The actuators 18 may be differently colored from the tray 10 (e.g., with at least a portion of the tray 10 being a first color and at least a portion of the actuators 18 being a second color that is brighter than the first color) to call attention to themselves. The actuators 18 may also (or alternatively) include indicia (e.g., an arrow) to suggest the way in which the actuator 18 is to be manipulated to eject the medication 16. It may be advantageous for the portion of the actuator 18 to be manipulated (i.e., the external portion 50 in the illustrated embodiment) to be larger than the associated cell 14 to make it easier for a subject with impaired dexterity and/or eyesight to access the medication 16 contained within the cell 14.

The host processor 36 detects that the switch 40 has changed from the first state to the second state and may take any of a number of actions in response. For example, the host processor 36 may include an internal, real-time clock 46 and record the time at which the state of the switch 40 changed (i.e., the time at which the medication 16 was accessed and ingested). This may be useful in allowing a medical professional to determine whether the subject is abiding by a prescribed medication routine. If the medication container 12 includes a plurality of cells 14, with the tray 10 including a plurality of switches 40, then the host processor 36 may be programmed to record the identity of the switch 40 that has changed its state, along with the sequence in which the states of the various switches 40 have changed. This may be especially advantageous if the different cells 40 contain different types and/or doses of medication 16, because a medical professional may use such information to determine whether the subject is ingesting the proper medication, in the proper order, and at the proper time.

If provided, a communication device 44 electrically coupled to the host processor 36 may transmit data from the host processor 36 to a separate electronic device, such as a central database, computer, tablet, or cellular telephone. If a communication device 44 is provided, then the separate electronic device with which it communicates may include an internal clock, thereby allowing for the host processor 36 to omit an internal real-time clock. In such an embodiment, the host processor 36 may be programmed to cooperate with the communication device 44 to immediately transmit data to a separate electronic device upon a switch 40 changing to the second state. The separate electronic device may record the time at which it receives a signal from the communication device 44, thereby allowing the time at which a dose of medication 16 was accessed to be determined without relying upon an internal clock of the host processor 36. In such an embodiment, the host processor 36 may be configured to operate in a relatively low power state and be programmed to transition from the relatively low power state to a higher power state upon determining that a switch 40 has changed to its second state, with the host processor 36 in the higher power state cooperating with the communication device 44 to transmit one or more signals to a separate electronic device.

In an alternative embodiment, rather than the host processor 36 and communication device 44 pushing signals to a separate electronic device, the host processor 36 may be programmed to record and retain data until the communication device 44 receives a signal or command from a separate electronic device to request data from the host processor 36. The host processor 36 may be configured to operate in the aforementioned relatively low power state before the communication device 44 receives a signal from a separate electronic device, with the host processor 36 transitioning to its higher power state upon the communication device 44 receiving a signal from a separate electronic device. Data may be transferred between the tray 10 and a separate electronic device by any suitable means, such as wirelessly (e.g., via near field communication, Bluetooth, WiFi, etc.) or via contact between portions of the separate electronic device and tray 10 (e.g., USB ports).

The host processor 36 may be programmed with particular information (e.g., the time at which a particular medication 16 is to be accessed or the sequence in which a plurality of actuators 18 are to be manipulated), which the host processor 36 may compare to the information gathered upon a switch 40 changing to the second state. This may be programmed into the host processor 36 at any suitable time, such as being downloaded by the host processor 36 around the time that the medication container 12 is inserted into the tray 10. Alternatively, the host processor 36 may omit such programming and instead only record data, rather than also comparing the data to prescribed values. If the host processor 36 is programmed with data regarding the time at which a particular dose of medication 16 is to be ingested and includes a real-time clock 46, it may compare the time at which the switch 40 changed to the second state to a preselected time (corresponding to the time at which the medication 16 is scheduled to be ingested) to determine whether the medication 16 was accessed before the prescribed time. If the medication 16 was accessed using the actuator 18 before the prescribed time, then the host processor 36 may cooperate with the communication device 44 to alert a medical professional of this irregularity.

Figure 3:
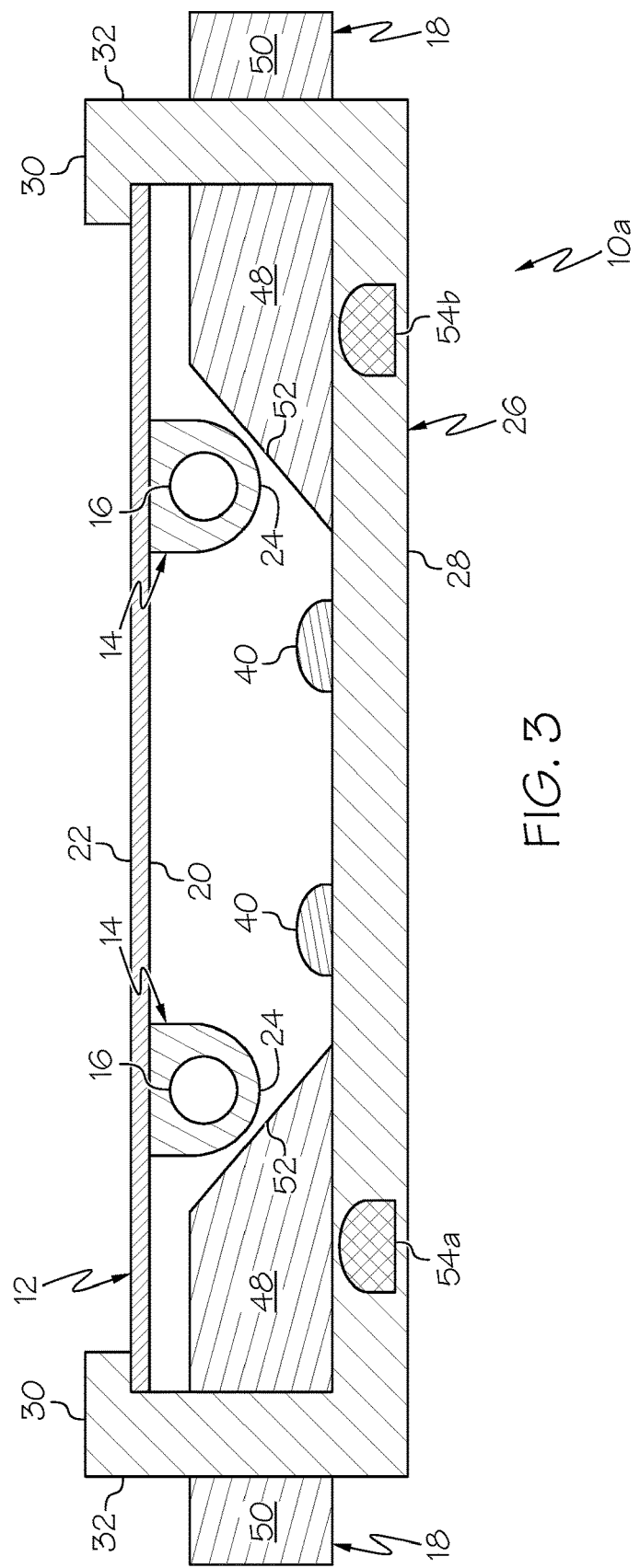
FIG. 3 is a front cross-sectional view of an alternative embodiment of a smart ejection tray and associated medication container according to the present disclosure.
Figure 4:
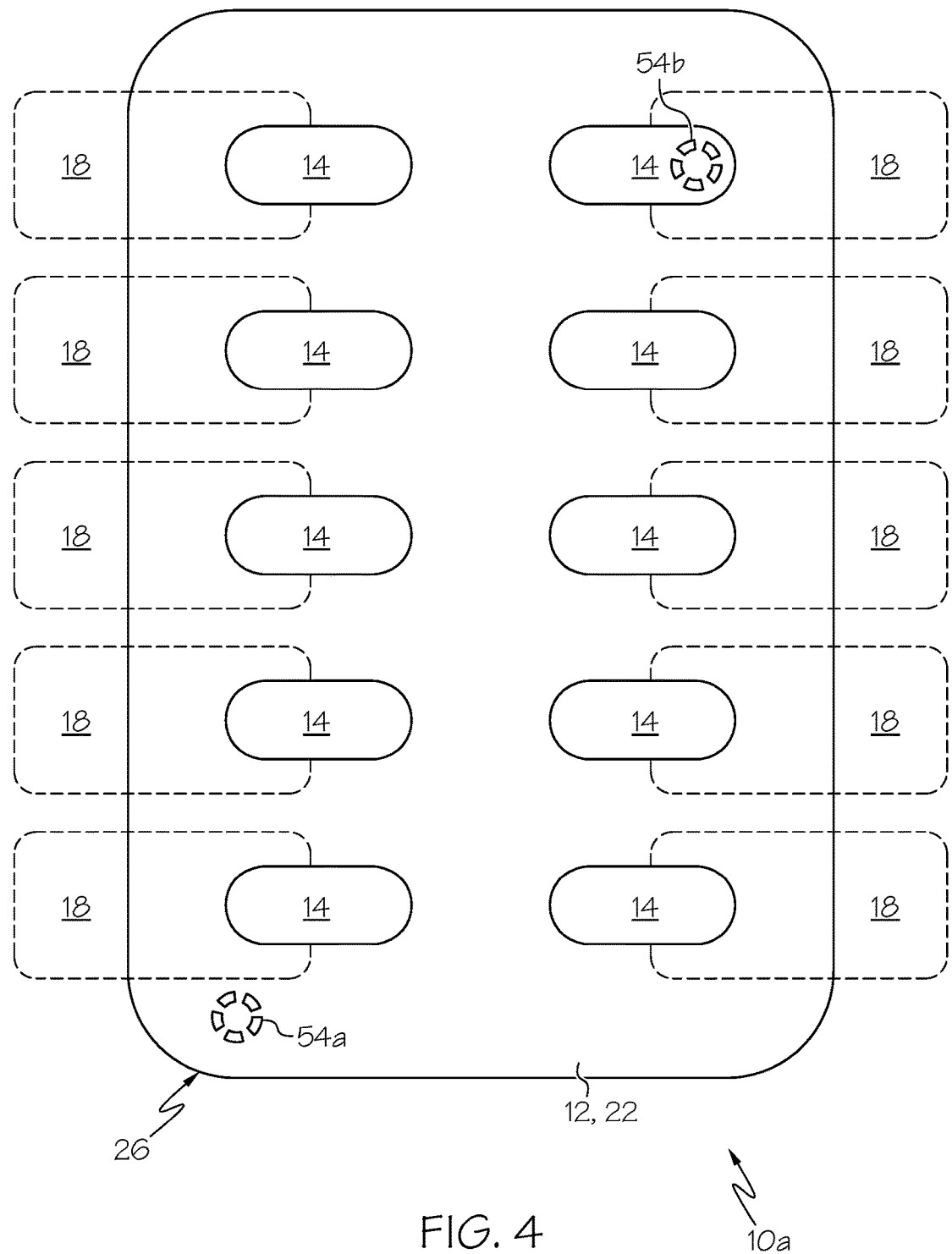
FIG. 4 is a top plan view of the ejection tray and medication container of FIG. 3.

Additionally, if the host processor 36 is programmed with data regarding the time at which a particular dose of medication 16 is to be ingested and includes a real-time clock 46, it may be advantageous for the tray 10a to be provided with at least one indicator 54a, 54b electrically coupled to the host processor 36 (FIGS. 3 and 4). The circuit 34 of tray 10a of FIGS. 3 and 4 is not illustrated, but it should be understood that the tray 10a of FIGS. 3 and 4 may be provided according to the foregoing description of the tray 10 of FIGS. 1 and 2, except with the additional provision of one or more indicators 54a, 54b and any design changes necessary to support such indicators 54a, 54b (e.g., additional conductors 38 electrically coupling the indicator(s) 54a, 54b to the host processor 36).

The indicator 54a, 54b, if provided, is configured to alert a subject that it is time for an actuator 18 associated with the indicator 54a, 54b to be manipulated. FIG. 3 shows two indicators 54a and 54b associated with the bottom surface 28 of the tray frame 26, but an indicator may be associated with some other portion of the tray 10a without departing from the scope of the present disclosure. While FIGS. 3 and 4 show two indicators 54a and 54b, it is within the scope of the present disclosure for a tray 10a to have any number of indicators. However, in a preferred embodiment, a tray 10a has the same number of actuators 18 and indicators 54a, 54b, with each actuator 18 having a different indicator 54a, 54b associated therewith. If more than one indicator 54a, 54b is provided, then all of the indicators 54a, 54b may be substantially identical or they may be differently configured and/or oriented.

In the illustrated embodiment, each indicator 54a, 54b is provided as a light (e.g., a light-emitting diode), which provides the subject with a visual cue when the indicator 54a, 54b has been activated by the host processor 36. In other embodiments, the indicator(s) of a tray may be differently configured and provide a non-visual cue (or a combination of types of cues, such as audible and/or tactile) when the indicator has been activated by the host processor. Regardless of the particular configuration of the indicator, it is configured to change from a first state to a second state upon receiving an appropriate signal from the host processor 36. The first state may be considered a "dormant" state (with the indicator being unlit if it is provided as a light), which signifies that it is not time for the subject to manipulate the associated actuator 18 and ingest the associated dose of medication 16. When the host processor 36 determines that it is time for the subject to ingest the medication 16 associated with a particular actuator 18 (e.g., when the time indicated by the real-time clock 46 of the host processor 36 is equal to a preselected time), it may send a signal or command to the indicator 54a, 54b associated with that actuator 18, which causes the indicator 54a, 54b to change to its second or "active" state. In the active state, the indicator 54a, 54b provides some cue to the subject (e.g., by becoming lit when the indicator 54a, 54b is a light) that the actuator 18 associated with the indicator 54a, 54b is to be manipulated to access the associated dose of medication 16. Preferably, the host processor 36 is programmed to cause the indicator 54a, 54b to change from the second state to the first state upon determining that the appropriate actuator 18 has been used to eject a dose of medication 16 so that only one indicator 54a, 54b is ever in the second state at a time.

One of the illustrated indicators 54a is positioned adjacent to or laterally offset from an associated actuator 18 (FIG. 4). If an indicator 54a, 54b is configured to provide a subject with a visual cue and is associated with the bottom surface 28 of the tray frame 26 (as illustrated), then it may be advantageous for the medication container 12 to be at least partially light-transmissive, which allows a subject to see the indicator 54a, 54b through the medication container 12. Alternatively, if the medication container 12 is not light-transmissive, then it may be advantageous for the indicator 54a, 54b to be placed at a location that is not obscured by the medication container 12 (e.g., at the top surface 30 of the frame 26).

The other illustrated indicator 54b is shown in FIG. 3 as associated with the bottom surface 28 of the tray frame 26, while FIG. 4 shows that the associated actuator 18 overlays at least a portion of the indicator 54b. If the indicator 54b is configured to provide a subject with a visual cue and is positioned beneath the associated actuator 18, then it may be advantageous for the indicator 54b to cause the appearance of the actuator 18 to change when the indicator 54b is in its second state. For example, if the indicator 54b is a light that is configured to become illuminated in the second state, then the actuator 18 (or at least a portion thereof) may be configured to glow or otherwise respond to the light from the indicator 18 by taking on an appearance that is distinct from the appearance of the other actuators 18 of the tray 10a. This may be especially advantageous if the indicator 54b is positioned beneath the associated cell 14 and medication 16, which may prevent a subject from directly seeing the indicator 54b.

Figure 5:
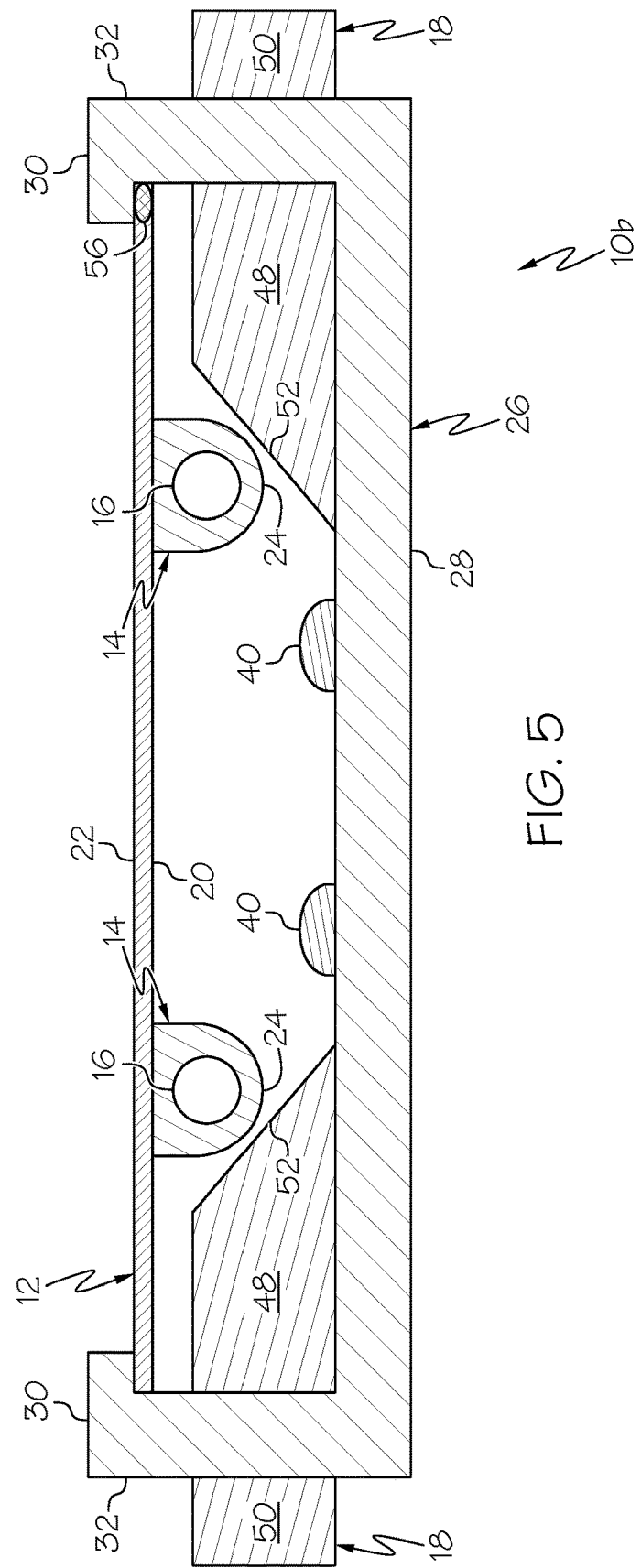
FIG. 5 is a front cross-sectional view of another alternative embodiment of a smart ejection tray and associated medication container according to the present disclosure.

As described above, it is intended for a user to access the medication 16 inside of a cell 14 by using an actuator 18 of the tray 10, 10a. However, it may be possible for a subject to instead access the medication 16 without manipulating the associated cell XX. In particular, it is possible for the cell 14 to remain untouched, while the cover 22 is directly engaged and broken or manipulated to remove medication 16 from the cell 14. Such use tends to circumvent the intended means for assuring proper medication compliance of the embodiments of FIGS. 1-4, in which case additional or alternative means may be provided for monitoring this misuse of the medication container 12. FIG. 5 shows an exemplary smart tray 10b (which may be provided according to the above description of the embodiments of FIGS. 1-4), but with an additional switch or sensor 56 associated with the frame 26, which provides an anti-tamper function. FIG. 5 illustrates a single sensor 56, but it is within the scope of the present disclosure for a plurality of sensors 56 to be provided.

In the embodiment of FIG. 5, the sensor 56 is associated with the top surface 30 of the tray frame 26, facing the open interior of the frame 26, in which the medication container 12 is positioned. The sensor 56 is in contact with the cover 22 of the medication container 12 and electrically coupled to the host processor 36 (e.g., by a conductor 38 of the type described above with respect to the embodiment of FIGS. 1 and 2). In one embodiment, the sensor 56 is configured to (in a first state) provide a default signal to the host processor 36, which signifies that the cover 22 of the medication container 12 is intact or still enclosing medication 16 within a cell 14. When medication 16 has been accessed through the cover 22, the sensor 56 may change to a second state and provide the host processor 36 with a different signal (or with no signal whatsoever), which signifies that the medication 16 has been accessed through the cover 22. In another embodiment, the sensor 56 may be configured to (in a first state) provide no signal to the host processor 36, signifying that the cover 22 of the medication container 12 is intact or still enclosing medication 16 within a cell 14. When medication 16 has been accessed through the cover 22, the sensor 56 may change to a second state and provide the host processor 36 with a signal, which signifies that the medication 16 has been accessed.

Upon determining that the sensor 56 has changed to the second state, the host processor 36 may carry out any of a number of responses. In one embodiment, the host processor 36 may determine whether the switch 40 associated with the cell 14 is also in the second state. If the switch 40 is in the second state, it is an indication that the actuator 18 was used to eject the medication 16 (i.e., that the tray 10b was used properly). On the other hand, if the switch 40 is still in the first state, it is an indication that the medication 16 was accessed by directly manipulating the cover 22 of the medication container 12 (i.e., that the tray 10b was not used properly). If the host processor 36 includes a real-time clock 46 and has determined that the cover 22 was manipulated to access the medication 16, then the host processor 36 may compare the time at which the sensor 56 changed to the second state to a preselected time (corresponding to the time at which the medication 16 is scheduled to be ingested) to determine whether the medication 16 was accessed before the prescribed time. If the cover 22 of the medication container 12 was directly manipulated to access the medication 16 before the prescribed time, then the host processor 36 may cooperate with the communication device 44 to alert a medical professional. Even if the medication 16 was accessed at the proper time, it may be advantageous for the host processor 36 and communication device 44 to cooperate to alert a medical professional, who may desire to counsel the subject on how to properly access the medication 16 (i.e., by using the associated actuator 18).

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. An ejection tray for use in combination with a medication container including a medication-containing cell, comprising:
a frame configured to receive at least a portion of a medication container including a medication-containing cell;
an actuator movably associated with the frame to eject the medication from the cell;
a switch associated with the frame and configured to change from a first state to a second state upon the actuator being moved to eject the medication from the cell;
a host processor associated with the frame, electrically coupled or selectively coupled to the switch, and programmed to detect a change in the state of the switch, the host processor is configured to operate in a first state and upon detecting a change in the state of the switch, transition to a second state, and the host processor cooperates with the communication device to transmit data to a separate electronic device; and
where the host processor is programmed to record an identity of the switch that has changed its state;
a communication device associated with the frame, electrically coupled to the host processor, and configured to communicate with a separate electronic device and the host processor is programmed to cooperate with the communication device to transmit data to a separate electronic device upon the communication device receiving a signal from the separate electronic device, and
the medication container includes a plurality of medication-containing cells and the ejection tray includes a plurality of actuators and switches, and each actuator is associated with a different one of the switches, is configured to be associated with a different one of the cells of the medication container, and movably associated with the frame to eject the medication from the associated cell and the ejection tray sized and configured such that the tray clips onto or around the medication container.

2. The ejection tray of claim 1, wherein the host processor is programmed to record the time at which the state of the switch changes.

3. The ejection tray of claim 1, wherein each switch is electrically coupled or selectively coupled to the host processor and configured to change from said first state to said second state upon the associated actuator being moved to eject the medication from the associated cell, and
the host processor is programmed to detect a change in the state of any of the switches.

4. The ejection tray of claim 3, wherein the host processor is programmed with a sequence in which the actuators are to be moved to eject medication from the associated cells.

5. The ejection tray of claim 3, wherein all of the actuators are movable in a common plane.

6. The ejection tray of claim 1, wherein the host processor is programmed to cooperate with the communication device to transmit data to a separate electronic device without the communication device receiving a signal from said separate electronic device.

7. The ejection tray of claim 1, wherein the first state is a relatively low power state and the second state is a higher power state.

8. The ejection tray of claim 1, wherein the communication device is configured to communicate wirelessly with a separate electronic device.

9. The ejection tray of claim 1, wherein the communication device is configured to communicate with a separate electronic device upon physical contact between the ejection tray and the separate electronic device.

10. The ejection tray of claim 1, wherein at least a portion of the tray is a first color and at least a portion of the actuator is a second color.

11. The ejection tray of claim 1, further comprising an indicator associated with the frame, electrically coupled to the host processor, and configured to change from a first state to a second state to indicate that the actuator is to be moved to eject the medication from the cell.

12. The ejection tray of claim 11, wherein the host processor includes a real-time clock and the host processor is programmed to cause the indicator to change from the first state to the second state upon the host processor determining that the time indicated by the real-time clock is equal to a preselected time.

13. The ejection tray of claim 11, wherein the indicator is laterally offset from the actuator.

14. The ejection tray of claim 11, wherein the actuator overlays at least a portion of the indicator.

15. The ejection tray of claim 1, configured for use in combination with a medication container including a cover overlaying the cell, and further comprising a sensor associated with the frame, electrically coupled to the host processor, and configured to detect whether the medication has been accessed through the cover without use of the actuator.

16. The ejection tray of claim 15, wherein the host processor includes a real-time clock and the host processor is programmed to compare the time at which the sensor determines that the medication has been accessed through the cover to determine whether the medication has been accessed before a preselected time.

17. The ejection tray of claim 1, configured to be reused with more than one medication container.

\* \* \* \* \*